United States Patent [19]

Shono et al.

[11] 4,059,595

[45] Nov. 22, 1977

[54] PROCESS FOR PREPARING 3-OXY-4H-PYRAN-4-ONE DERIVATIVES

[75] Inventors: Tatsuya Shono, Kyoto; Yoshihiro Matsumura, Takatsuki, both of Japan

[73] Assignee: Otsuka Kagaku Yakuhin Kabushiki Kaishi, Osaka, Japan

[21] Appl. No.: 661,823

[22] Filed: Feb. 26, 1976

[30] Foreign Application Priority Data

July 17, 1975 Japan .................................. 50-87940

[51] Int. Cl.$^2$ ........................................... C07D 309/22
[52] U.S. Cl. ...................... 260/345.9 R; 260/345.8 R; 260/347.8
[58] Field of Search ........................... 260/345.9, 345.8

[56] References Cited

U.S. PATENT DOCUMENTS

3,476,778  11/1969  Schleppnik et al. .............. 260/345.8

OTHER PUBLICATIONS

Shono et al., Tetrahedron Letters, No. 17, pp. 1363–1364 (1976).

*Primary Examiner*—Bernard Helfin
*Assistant Examiner*—Nicky Chan
*Attorney, Agent, or Firm*—Armstrong, Nikaido & Marmelstein

[57] ABSTRACT

A process for preparing a 3-oxy-4H-pyran-4-one derivative which comprises the steps of:
1. epoxidizing a 3-oxo-3,6-dihydro-2H-pyran derivative with a peroxide to obtain a 4,5-epoxy-3-oxotetrahydropyran derivative, and
2. heating the 4,5-epoxy-3-oxotetrahydropyran derivative.

10 Claims, No Drawings

PROCESS FOR PREPARING 3-OXY-4H-PYRAN-4-ONE DERIVATIVES

This invention relates to a novel process for preparing 3-oxy-4H-pyran-4-one derivatives.

3-Oxy-4H-pyran-4-one derivatives are useful as flavorings to be added to foods. For example, 2-methyl-3-oxy-4-H-pyran-4-one and 2-ethyl-3-oxy-4H-pyran-4-one are well-known flavorings. Thus the derivatives are very important as agents for improving the taste and flavor of foods, and various processes have been reported for the preparation of these derivatives as disclosed in Japanese patent publications No. 110/67, No. 6813/70, 17237/71 and 14105/72, J. Am. Chem. Soc. 68, 2557-61 (1946), 69, 2908-9 (1947), 70, 2321-5 (1948) and 73, 5912-13 (1951), etc. However, the proposed processes are not economical, because they use materials which are not readily available and involve cumbersome procedures leading to low yields. That is to say, these processes resort to the technique of treating 4H-pyran-4-one derivatives used as the starting material and intermediate, involve a great number of reaction steps and produce large amounts of by-products, substantially based on the conventional concept of synthesis. Further these conventional methods are conducted, for example, at elevated temperatures of about 200° to 600° C and involve problems such as the disposal of heavy metals used as catalysts in the reactions and fermantation residue formed, etc, creating serious environmental problems.

An object of this invention is to provide a novel and advantageous process for preparing 3-oxy-4H-pyran-4-one derivatives.

Another object of this invention is to provide a process for preparing 3-oxy-4H-pyran-4-one derivatives which process involves reduced number of reaction steps and easy procedures under mild reaction conditions.

Another object of this invention is to provide a process for preparing 3-oxy-4H-pyran-4-one derivatives which process entails small amounts of by-products.

Another object of this invention is to provide a process for preparing 3-oxy-4H-pyran-4-one derivatives from a readily available starting material.

Another object of this invention is to provide a process for preparing 3-oxy-4H-pyran-4-one derivatives with reduced possibility of pollution, without using any chemicals which would pose environmental problems.

These and other objects of this invention will become apparent from the following description.

The process of this invention for preparing a 3-oxy-4H-pyran-4-one derivative comprises the steps of epoxidizing a 3-oxo-3,6-dihydro-2H-pyran derivative represented by the formula

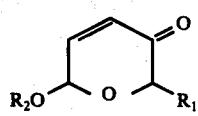

wherein $R_1$ is hydrogen atom or straight-chain or branched-chain alkyl having 1 to 10 carbon atoms, and $R_2$ is hydrogen atom, straight-chain or branched-chain alkyl having 1 to 6 carbon atoms or straight-chain or branched-chain acyl having 1 to 6 carbon atoms with a peroxide, and heating the resulting 4,5-epoxy-3-oxotetrahydropyran derivative represented by the formula

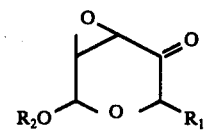

wherein $R_1$ and $R_2$ are as defined above, the 3-oxy-4H-pyran-4-one derivative being represented by the formula

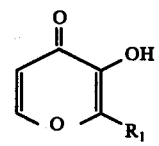

wherein $R_1$ is as defined above.

We have found that the desired compounds of this invention can be prepared advantageously, free of the conventional problems described above, by epoxidizing a 2H-pyran-3-one derivative, which can be readily derived from furfural, and further heating the resulting epoxidized 3-oxotetrahydropyran derivative.

The starting material of this invention, namely 3-oxo-3,6-dihydro-2H-pyran derivative (1) (hereinafter referred to as "$\alpha,\beta$-unsaturated ketone") is a known compound and is readily prepared, for example, by the following reaction in a high yield.

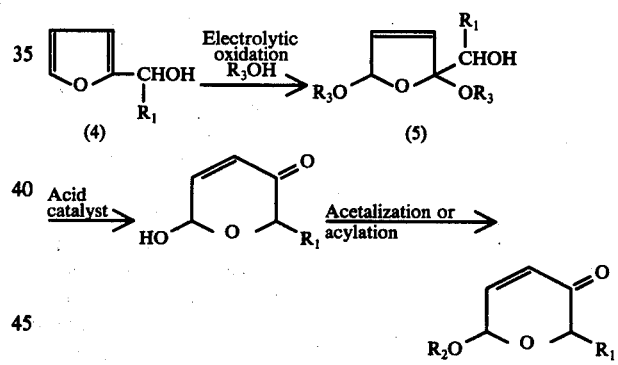

In the formulae, $R_1$ and $R_2$ are as defined above, and $R_3$ is straight-chain or branched-chain alkyl having 1 to 4 carbon atoms.

Thus 6-hydroxy-3-oxo-3,6-dihydro-2H-pyran derivative is produced by electrolytically oxidizing furfuryl alcohol (4) in the presence of $R_3OH$ to obtain 2,5-dialkoxy-furfuryl alcohol (5) and treating the alcohol with an acid catalyst to enlarge the ring, and 6-alkoxy or 6-acyloxy-3-oxo-3,6-dihydro-2H-pyran derivative is prepared by subjecting above 6-hydroxy derivative to subsequent acetalization or acylation.

According to this invention, 6-hydroxy-3-oxo-3,6-dihydro-2H-pyran derivative and 6-alkoxy- or 6-acyloxy-3-oxo-3,6-dihydro-2H-pyran derivative are usable as starting materials as shown above. However, the latter 6-alkoxy- or 6-acyloxy-3-oxo-3,6-dihydro-2H-pyran derivative is more chemically stable and therefore more preferable than the former 6-hydroxy derivative. Although acetalization and acylation of this invention can be conducted by a usual method, we have found a method, more advantageous than the conventional methods, of converting the former 6-hydroxy derivative to the latter 6-alkoxy derivative as will be described below.

The 6-alkoxy derivative is obtained by the acetalization of 6-hydroxy derivative. The acetalization is heretofore effected for example by the method disclosed in Tetrahedron, 27, 1973-1996 (1971) which method requires use of a strong Lewis acid such as tin tetrachloride or boron trifluoride as a catalyst and a low reaction temperature of up to 0° C and yet attains low yields. In view of these drawbacks, we have conducted extensive research and found a method by which the desired product can be obtained in high yields under mild reaction conditions. According to this method, the reaction is conducted in a solvent with heating, using orthoformate or aliphatic alcohol as the acetalizing agent and a weak Lewis acid as a catalyst. Examples of orthoformates are methyl orthoformate, ethyl orthoformate, propyl orthoformate, butyl orthoformate, etc. and examples of aliphatic alcohols are methanol, ethanol, isopropanol, butanol, etc. Exemplary of the weak Lewis acid to be used for the reaction are calcium chloride, ammonium chloride, zinc chloride, potassium chloride, magnesium chloride, magnesium sulfate, calcium sulfate, ammonium nitrate, sodium nitrate, etc. Useful solvents include diethyl ether, diisopropyl ether and like aliphatic ethers; tetrahydrofuran, dioxane and like cyclic ethers; methylene chloride, chloroform, carbon tetrachloride and like hydrocarbon halides; benzene, toluene, xylene and like aromatic hydrocarbons; etc. The amount of acetalizing agent to be used for the reaction is usually about 0.5 to 10 moles, preferably about 0.6 to 2 moles, per mole of the starting material, i.e. 6-hydroxy-3-oxo-3,6-dihydro-2H-pyran derivative. The amount of catalyst is usually about 0.05 to 1 mole, preferably about 0.1 to 0.3 mole, per mole of the starting material. The reaction temperature which may be dependent on the particular solvent used is generally about 30° to 150° C, preferably about 50° to 80° C. The acylating reaction for preparing 6-acyloxy-3-oxo-3,6-dihydro-2H-pyran derivative from 6-hydroxy-3-oxo-3,6-dihydro-2H-pyran derivative can be conducted by a conventional method, namely by reacting the starting material with an acylating agent in a solvent in the presence of a catalyst. Examples of useful acylating agents are carboxylic anhydrides such as acetic anhydride, propionic anhydride, butyric anhydride and the like and acyl halide compounds such as acetyl chloride, propionyl chloride, butyryl chloride and bromides corresponding to these chlorides. Examples of catalysts are pyridine, piperidine, triethylamine, phosphorus pentoxide, etc. Useful solvents are those enumerated for use in the acetalization reaction. The amount of the acylating agent to be used for the reaction may preferably be about 1 to 1.5 moles per mole of the starting material. The reaction temperature is usually about −10° to 50° C, preferably about 0° to 30° C.

Examples of α,β-unsaturated ketones (1) of this invention are 6-hydroxy-3-oxo-3,6-dihydro-2H-pyran, 6-methoxy-3-oxo-3,6-dihydro-2H-pyran, 6-ethoxy-3-oxo-3,6-dihydro-2H-pyran, 6-isopropoxy-3-oxo-3,6-dihydro-2H-pyran, 6-butoxy-3-oxo-3,6-dihydro-2H-pyran, 6-acetoxy-3-oxo-3,6-dihydro-2H-pyran, 2-methyl-6-hydroxy-3-oxo-3,6-dihydro-2H-pyran, 2-methyl-6-methoxy-3-oxo-3,6-dihydro-2H-pyran, 2-methyl-6-ethoxy-3-oxo-3,6-dihydro-2H-pyran, 2-methyl-6-isopropoxy-3-oxo-3,6-dihydro-2H-pyran, 2-methyl-6-butoxy-3-oxo-3,6-dihydro-2H-pyran, 2-methyl-6-acetoxy-3-oxo-3,6-dihydro-2H-pyran, 2-methyl-6-isobutoxy-3-oxo-3,6-dihydro-2H-pyran, 2-methyl-6-caproxy-3-oxo-3,6-dihydro-2H-pyran, 2-ethyl-6-methoxy-3-oxo-3,6-dihydro-2H-pyran, 2-ethyl-6-ethoxy-3-oxo-3,6-dihydro-2H-pyran, 2-ethyl-6-isopropoxy-3-oxo-3,6-dihydro-2H-pyran, 2-ethyl-6-pentyloxy-3-oxo-3,6-dihydro-2H-pyran, 2-ethyl-6-hexyloxy-3-oxo-3,6-dihydro-2H-pyran, 2-isopropyl-6-methoxy-3-oxo-3,6-dihydro-2H-pyran, 2-isopropyl-6-ethoxy-3-oxo-3,6-dihydro-2H-pyran, 2-isopropyl-6-acetoxy-3-oxo-3,6-dihydro-2H-pyran, 2-butyl-6-methoxy-3-oxo-3,6-dihydro-2-H-pyran, 2-butyl-6-ethoxy-3-oxo-3,6-dihydro-2H-pyran, 2-butyl-6-acetoxy-3-oxo-3,6-dihydro-2H-pyran, 2-hexyl-6-methoxy-3-oxo-3,6-dihydro-2H-pyran, 2-hexyl-6-ethoxy-3-oxo-3,6-dihydro-2H-pyran, 2-hexyl-6-acetoxy-3-oxo-3,6-dihydro-2H-pyran, 2-octyl-6-methoxy-3-oxo-3,6-dihydro-2H-pyran, 2-octyl-6-ethoxy-3-oxo-3,6-dihydro-2H-pyran, 2-octyl-6-acetoxy-3-oxo-3,6-dihydro-2H-pyran, 2-decyl-6-methoxy-3-oxo-3,6-dihydro-2H-pyran, 2-decyl-6-ethoxy-3-oxo-3,6-dihydro-2H-pyran, 2-decyl-6-acetoxy-3-oxo-3,6-dihydro-2H-pyran, etc.

According to this invention, 4,5-epoxy-3-oxotetrahydropyran derivative (2) (hereinafter referred to as "epoxy ketone") is prepared by epoxidizing the α,β-unsaturated ketone (1) with a peroxide. The compound (1), the starting material, has a very complex structure of cyclic ether wherein the oxygen atom forms part of acetal. Although it has been almost unknown to epoxidize such α,β-unsaturated ketone, we have succeeded in readily epoxidizing the ketone by treating the ketone with a peroxide under the conditions to be described below. Useful peroxides for the reaction are, for example, those generally known such as hydrogen peroxide, trifluoroperacetic acid, perbenzoic acid, monochloroperbenzoic acid, monoperphthalic acid, tertiary butylhydroperoxide, ditertiary butyl peroxide, etc. It is preferable to conduct the epoxidizing reaction of this invention in the presence of at least one alkaline substance such as sodium hydroxide, potassium hydroxide, sodium carbonate, potassium carbonate, basic ion-exchange resin or the like. The epoxidizing reaction can be effected in the absence or presence of solvent. Examples of useful solvents are water; alcohols such as methanol, ethanol, isopropanol, etc.; lower aliphatic organic acids such as acetic acid, propionic acid, etc.; aliphatic ethers such as diethyl ether, diisopropyl ether, methyl cellosolve, ethyl cellosolve, etc.; cyclic ethers such as tetrahydrofuran, dioxane, etc.; esters such as ethyl acetate, butyl acetate, etc.; and hydrocarbon halides such as methylene chloride, chloroform, carbon tetrachloride, etc. The amount of peroxide to be used for the reaction is usually about 0.5 to 3 moles, preferably about 1 to 2 moles, per mole of the α,β-unsaturated ketone. The amount of alkaline substance to be used for the reaction is usually about 0.1 to 1 mole, preferably about 0.2 to 0.5 mole, per mole of the α,β-unsaturated ketone. The reaction is conducted at a temperature of about −30° to 40° C, preferably at about −20° to 20° C. After the completion of the reaction, the reaction mixture may further be subjected to separation and recovery steps. When some peroxide remains unreacted, it is preferable to add, for example, a sodium thiosulfate solution to the mixture to inactivate the peroxide and to thereby eliminate the possible hazard of explosion during the subsequent treatment.

The reaction mixture is washed with water, the oily layer obtained is distilled to remove the solvent and the resulting oily product may be subjected directly to the subsequent reaction. Alternatively the oily product may be distilled in vacuum or subjected to column chromatography to obtain purified epoxy ketone, which may be used for the subsequent reaction. It is preferable to use the isolated purified epoxy ketone for the following reaction to render the subsequent treatment easier. Examples of epoxy ketones (2) obtained from the reaction described above are 6-hydroxy-4,5-epoxy-3-oxotetrahydropyran, 6-methoxy-4,5-epoxy-3-oxotetrahydropyran, 6-ethoxy-4,5-epoxy-3-oxotetrahydropyran, 6-isopropoxy-4,5-epoxy-3-oxotetrahydropyran, 6-butoxy-4,5-epoxy-3-oxotetrahydropyran, 6-acetoxy-4,5-epoxy-3-oxotetrahydropyran, 6-hydroxy-4,5-epoxy-3-oxo-2-methyltetrahydropyran, 6-methoxy-4,5-epoxy-3-oxo-2-methyltetrahydropyran, 6-ethoxy-4,5-epoxy-3-oxo-2-methyltetrahydropyran, 6-isopropoxy-4,5-epoxy-3-oxo-2-methyltetrahydropyran, 6-butoxy-4,5-epoxy-3-oxo-2-methyltetrahydropyran, 6-acetoxy-4,5-epoxy-3-oxo-2-methyltetrahydropyran, 6-isobutyryloxy-4,5-epoxy-3-oxo-2-methyltetrahydropyran, 6-caproxy-4,5-epoxy-3-oxo-2-methyltetrahydropyran, 6-methoxy-4,5-epoxy-3-oxo-2-ethyltetrahydropyran, 6-ethoxy-4,5-epoxy-3-oxo-2-ethyltetrahydropyran, 6-isopropoxy-4,5-epoxy-3-oxo-2-ethyltetrahydropyran, 6-pentyloxy-4,5-epoxy-3-oxo-2-ethyltetrahydropyran, 6-hexyloxy-4,5-epoxy-3-oxo-2-ethyltetrahydropyran, 6-methoxy-4,5-epoxy-3-oxo-2-isopropyltetrahydropyran, 6-ethoxy-4,5-epoxy-3-oxo-2-isopropyltetrahydropyran, 6-acetoxy-4,5-epoxy-3-oxo-2-isopropyltetrahydropyran, 6-methoxy-4,5-epoxy-3-oxo-2-butyltetrahydropyran, 6-ethoxy-4,5-epoxy-3-oxo-2-butyltetrahydropyran, 6-acetoxy-4,5-epoxy-3-oxo-2-butyl-tetrahydropyran, 6-methoxy-4,5-epoxy-3-oxo-2-hexyltetrahydropyran, 6-ethoxy-4,5-epoxy-3-oxo-2-hexyltetrahydropyran, 6-acetoxy-4,5-epoxy-3-oxo-2-hexyltetrahydropyran, 6-methoxy-4,5-epoxy-3-oxo-2-octyltetrahydropyran, 6-ethoxy-4,5-epoxy-3-oxo-2-octyltetrahydropyran, 6-acetoxy-4,5-epoxy-3-oxo-2-octyltetrahydropyran, 6-methoxy-4,5-epoxy-3-oxo-2-decyltetrahydropyran, 6-ethoxy-4,5-epoxy-3-oxo-2-decyltetrahydropyran, 6-acetoxy-4,5-epoxy-3-oxo-2-decyltetrahydropyran, etc.

The 3-oxy-4H-pyran-4-one derivative (3), the desired product of this invention is readily obtained by heating the epoxy ketone (2). The conversion of the epoxy ketone (2) into the 3-oxy-4H-pyran-4-one derivative by the action of heat and acid is an entirely novel behavior as distinct from the usual ring cleavage of epoxy compounds due to hydrolysis. It is a novel reaction found by the present inventors for the first time. The reaction proceeds in the absence of catalyst but may preferably be effected in the presence of acid catalyst such as sulfuric acid, hydrochloric acid, hydrobromic acid or like inorganic acid, formic acid, acetic acid, propionic acid or like organic acid, methanesulfonic acid, benzenesulfonic acid, paratoluenesulfonic acid or like sulfonic acid, boron trifluoride, aluminum chloride, zinc chloride, titanium tetrachloride, antimony pentachloride, tin tetrachloride or like Lewis acid, or acid ion-exchange resin. Preferable acid catalysts are sulfuric acid, benzenesulfonic acid, paratoluenesulfonic acid and acid ion-exchange resin. The concentration of the acid itself to be used for the reaction may be usually about 10 to 100% by weight, preferably about 60 to 90% by weight, although variable with the kind of acid used. The concentration of the catalyst in the reaction system may be usually about 0.5 to 10 w/v %, preferably about 1 to 5 w/v %. The reaction will proceed in the absence of solvent but may preferably be effected in the presence of solvent. Examples of useful solvents are water; methanol, ethanol, isopropanol and like aliphatic alcohols; acetic acid, propionic acid and like lower aliphatic organic acids; diethyl ether, diisopropyl ether, methyl cellosolve, ethyl cellosolve and like aliphatic ethers; tetrahydrofuran, dioxane and like cyclic ethers; methylene chloride, chloroform, carbon tetrachloride and like hydrocarbon halides. The reaction temperature may be about 0° to 150° C, preferably about 50° to 100° C.

The desired compound (3) obtained by the reaction of this invention can be easily separated and recovered in a usual manner, for example by subjecting the reaction product to vacuum distillation or column chromatography, or by concentrating the product and purifying the concentrate by sublimation. Examples of 3-oxy-4H-pyran-4-one derivatives thus obtained according to this invention are 3-oxy-4H pyran-4-one, 2-methyl-3-oxy-4H-pyran-4-one, 2-ethyl-3-oxy-4H-pyran-4-one, 2-n-propyl-3-oxy-4H-pyran-4-one, 2-isopropyl-3-oxy-4H-pyran-4-one, 2-n-butyl-3-oxy-4H-pyran-4-one, 2-isobutyl-3-oxy-4H-pyran-4-one, 2n-amyl-3-oxy-4H-pyran-4-one, 2-isoamyl-3-oxy-4H-pyran-4-one, 2-n-hexyl-3-oxy-4H-pyran-4-one, 2-n-heptyl-3-oxy-4H-pyran-4-one, 2n-octyl-3-oxy-4H-pyran-4-one, 2-(1-ethylhexyl)-3-oxy-4H-pyran-4-one, 2-n-nonyl-3-oxy-4H-pyran-4-one, 2-n-decyl-3-oxy-4H-pyran-4-one, etc.

The novel process of this invention uses a starting material which is not a naturally occurring substance but is a 2H-pyran-3-one derivative readily available from furfural, gives the desired product by a short two-step reaction which proceeds under mild conditions, does not involve use of any harmful substances and reduces the possibility of causing pollution. Thus the process produces the desired product at a very low cost because of high reaction yield and reduced number of steps.

Examples of this invention will be given below in which the percentages are all by weight.

EXAMPLE 1

A 12.8 g quantity of 2-methyl-6-hydroxy-3-oxo-3,6-dihydro-2H-pyran and 14.8 g of ethyl orthoformate are reacted in the presence of 1 g of zinc chloride in 100 ml of benzene with refluxing for 120 minutes. After the reaction, the benzene is distilled off, the residue is poured into 50 ml of water and the mixture is extracted three times with 50 ml portions of ether. The ethereal layer is washed with an aqueous solution of sodium carbonate and then dried over magnesium sulfate. After removing the magnesium sulfate, the dried mass is distilled to remove the ether, and the residue is distilled at a reduced pressure of 30 mm Hg to give 12 g of 2-methyl-6-ethoxy-3-oxo-3,6-dihydro-2H-pyran as a yellow liquid fraction at 82° to 85° C in a yield of 85%.

| Elementary analysis | C | H |
|---|---|---|
| Found: | 59.2% | 7.0% |
| Calcd: | 59.0 | 7.3 |

IR ($\nu$max cm$^{-1}$): 1696 (C=O), 1630 (C=C), 1050 (C—O—C).

UV [$\lambda$max($\epsilon$)]: 211, 278, 343.

EXAMPLE 2

A 14.2 g quantity of 2-ethyl-6-hydroxy-3-oxo-3,6-dihydro-2H-pyran and 50 g of methyl orthoformate are reacted in the presence of 10 g of magnesium sulfate under reflux for 24 hours. After the reaction, the mixture is filtered to remove the magnesium sulfate, and the filtrate is concentrated in vacuum to remove the excess methyl orthoformate. The residue is poured into 50 ml of water, the mixture is extracted with ether, and the ethereal layer is washed with a sodium carbonate solution and dried over magnesium sulfate. The dried mass is distilled to remove the ether, and the residue is further distilled at a reduced pressure of 12 mm Hg to give 13.4 g of 2-ethyl-6-methoxy-3-oxo-3,6-dihydro-2H-pyran as a yellow liquid fraction at 85° to 90° C in a yield of 86%.

| Elementary analysis | C | H |
|---|---|---|
| Found: | 61.3% | 7.5% |
| Calcd: | 61.5 | 7.6 |

IR ($\nu$max cm$^{-1}$): 1700 (C=O), 1630 (C=C), 1050 (C—O—C).
UV [∥max($\epsilon$)]: 211, 278, 343.

EXAMPLE 3

A 14.2 g quantity of 2-ethyl-6-hydroxy-3-oxo-3,6-dihydro-2H-pyran and 74 g of n-butyl alcohol are reacted in the presence of 10 g of magnesium sulfate with refluxing for 24 hours. After the reaction, the mixture is filtered to remove the magnesium sulfate, and the filtrate is concentrated at a reduced pressure to remove the excess n-butyl alcohol. The residue is further distilled at a reduced pressure of 5 mm Hg to give 16.2 g of 2-ethyl-6-n-butoxy-3-oxo-3,6-dihydro-2H-pyran as a yellow liquid fraction at 83° to 88° C in a yield of 82.2%.

| Elementary analysis | C | H |
|---|---|---|
| Found: | 66.7% | 9.1% |
| Calcd: | 66.6 | 9.0 |

IR ($\nu$max cm$^{-1}$): 1700 (C=O), 1630 (C=C), 1050 (C—O—C).
UV [$\lambda$max($\epsilon$)]: 215, 280, 350.

EXAMPLE 4

A 12.8 g quantity of 2-methyl-6-hydroxy-3-oxo-3,6-dihydro-2H-pyran and 25 ml of acetic anhydride are reacted in the presence of 12.5 ml of pyridine with stirring at room temperature for 4 hours. After the reaction, the mixture is concentrated, the residue is poured into ice water, and the mixture is extracted with 100 ml of ether. The ethereal layer is washed with an aqueous solution of sodium carbonate and then dried over magnesium sulfate. After removing the magnesium sulfate, the ethereal layer is concentrated, and the residue is distilled at a reduced pressure of 0.4 mm Hg to give 12.6 g of 2-methyl-6-acetoxy-3-oxo-3,6-dihydro-2H-pyran as a colorless liquid fraction at 80° to 83° C in a yield of 80%.

| Elementary analysis | C | H |
|---|---|---|
| Found: | 53.2% | 6.4% |
| Calcd: | 53.1 | 6.3 |

IR ($\nu$max cm$^{-1}$): 1754 (CO—O—), 1700 (C=O), 1630 (C=C), 1000 (C—O—C).
UV [$\lambda$max($\epsilon$)]: 216, 331.

EXAMPLE 5

A 14.2 g quantity of 2-ethyl-6-hydroxy-3-oxo-3,6-dihydro-2H-pyran and 9 g of pyridine are dissolved in 100 ml of ether, and 12 g of isovaleryl chloride is slowly added dropwise to the solution with stirring while cooling the solution to a temperature of about 5° C. The mixture is thereafter reacted at room temperature for 60 minutes. The resulting reaction mixture is filtered to remove pyridine hydrochloride, the mother liquor is concentrated, the residue is poured into ice water, and the mixture is neutralized with sodium carbonate and then extracted with 100 ml of ether. The ethereal layer is dried over magnesium sulfate and then concentrated. The residue is separated by column chromatography, using a mixture of benzene and ethyl acetate (4:1 in volume ratio) as a developer. Concentration of the solvent gives 18.6 g of residue in a yield of 82.4%.

| Elementary analysis | C | H |
|---|---|---|
| Found: | 63.9% | 8.0% |
| Calcd: | 63.7 | 7.9 |

IR ($\nu$max cm$^{-1}$): 1750 (CO—O—), 1700 (C=O), 1630 (C=C), 1000 (C—O—C).
UV [$\lambda$max($\epsilon$)]: 210, 337.

EXAMPLE 6

A 12.8 g quantity of 2-methyl-6-ethoxy-3-oxo-3,6-dihydro-2H-pyran, 13 g of 30% aqueous solution of hydrogen peroxide and 100 ml of methanol are cooled to a temperature of about 10° C with full stirring. A 10 ml quantity of 1% aqueous solution of sodium hydroxide is added dropwise to the solution over a period of 30 minutes. The mixture is thereafter allowed to react for 1 hour. After the reaction, sodium thiosulfate is added to the mixture to decompose the unreacted hydrogen peroxide. The reaction mixture is then concentrated at a reduced pressure, the residue is extracted with 100 ml portions of ether three times, and the ethereal layer is concentrated. The concentrate is subjected to silica gel column chromatography using a mixture of benzene and ethyl acetate (1:3 in volume ratio). Distillation of the solvent at a reduced pressure gives 11.6 g of the desired compound as a colorless liquid residue in a yield of 88.7%.

| Elementary analysis | C | H |
|---|---|---|
| Found: | 55.8% | 6.9% |
| Calcd: | 55.8 | 6.9 |

IR ($\nu$max cm$^{-1}$): 1730 (C=O), 1150, 1080, 980 (C—O—C).

EXAMPLE 7

A 15.6 g quantity of 2-ethyl-6-methoxy-3-oxo-3,6-dihydro-2H-pyran, 15 g of 30% aqueous solution of hydrogen peroxide and 100 ml of methanol are cooled to a temperature of about 10° C with full stirring. The same procedure as in Example 6 is thereafter followed to obtain a concentrate, which is then distilled at a reduced pressure of 3 mm Hg to give 14.8 g of 6-methoxy-4,5-epoxy-3-oxo-2-ethyltetrahydropyran as a colorless liquid fraction at 83° to 88° C in a yield of 86.3%.

| Elementary analysis | C | H |
|---|---|---|
| Found: | 55.8% | 7.0% |
| Calcd: | 55.8 | 6.9 |

IR ($\nu$max cm$^{-1}$): 1730 (C=O), 1150, 1083, 1000 (C—O—C).

EXAMPLE 8

A 24.4 g quantity of 2-octyl-6-ethoxy-3-oxo-3,6-dihydro-2H-pyran, 36 g of 25% solution of peracetic acid in acetic acid and 100 ml of methanol are cooled to a temperature of about 5° C with full stirring. A 15 ml quantity of 1% aqueous solution of sodium hydroxide is added dropwise to the resulting solution over a period of 30 minutes. The mixture is thereafter allowed to react for 2 hours. The same procedure as in Example 6 is subsequently followed to obtain a concentrate. The concentrate is subjected to silica gel column chromatography using a mixture of benzene and ethyl acetate (1:3 in volume ratio). Distillation of the solvent at a reduced pressure gives 20.1 g of the desired compound as a pale yellow liquid residue in a yield of 77.4%.

| Elementary analysis | C | H |
|---|---|---|
| Found: | 69.2% | 10.0% |
| Calcd: | 69.5 | 10.2 |

IR ($\nu$max cm$^{-1}$): 1730 (C=O), 1150, 1083, 1000 (C—O—C).

EXAMPLE 9

A 26.8 g quantity of 2-n-decyl-6-methoxy-3-oxo-3,6-dihydro-2H-pyran, 17.2 g of m-chloroperbenzoic acid and 100 ml of methanol are cooled to a temperature of about 5° C with full stirring. A 5 ml quantity of 1-N aqueous solution of sodium hydroxide is added dropwise to the resulting solution over a period of 30 minutes. The mixture is thereafter allowed to react for 2 hours. The same procedure as in Example 6 is subsequently followed to obtain a concentrate. The concentrate is subjected to silica gel column chromatography, using a mixture of benzene and ethyl acetate (1:3 in volume ratio). Distillation of the solvent at a reduced pressure gives 21.7 g of the desired compound as a pale yellow liquid residue in a yield of 76.7%.

| Elementary analysis | C | H |
|---|---|---|
| Found: | 65.2% | 9.2% |
| Calcd: | 64.9 | 8.9 |

IR ($\nu$max cm$^{-1}$): 1730 (C=O), 1150, 1083, 1000 (C—O—C).

EXAMPLE 10

A 19.8 g quantity of 2-methyl-6-isobutyryloxy-3-oxo-3,6-dihydro-2H-pyran, 13 g of 30% aqueous solution of hydrogen peroxide and 100 ml of methanol are cooled to a temperature of about 10° C with full stirring. A 10 ml quantity of 1% aqueous solution of sodium hydroxide is added dropwise to the resulting solution over a period of 30 minutes. The mixture is then allowed to react for 1 hour. The same procedure as in Example 6 is thereafter followed to obtain a concentrate, which is then subjected to silica gell column chromatography, using a benzene-ethyl acetate mixture. Distillation of the solvent at a reduced pressure gives 15.9 g of the desired compound as a colorless liquid residue in a yield of 74.5%.

| Elementary analysis | C | Z |
|---|---|---|
| Found: | 55.8% | 6.4% |
| Calcd: | 56.0 | 6.5 |

IR ($\nu$max cm$^{-1}$): 1750 (—CO—O), 1730 (C=O), 1150, 1080, 980 (C—O—C).

EXAMPLE 11

A 15.8 g quantity of 6-ethoxy-4,5-epoxy-3-oxo-2-methyltetrahydropyran is dissolved in 500 ml of dioxane, and 114 g of 80% aqueous solution of sulfuric acid is added dropwise to the solution with stirring. The mixture is then allowed to react for 1 hour with refluxing. The resulting reaction mixture is cooled to room temperature and neutralized with sodium carbonate. The precipitated sodium sulfate is filtered off, and the filtrate is concentrated at a reduced pressure to give brown crystals. The crystals are purified by sublimation to give 9.6 g of 2-methyl-3-oxy-4H-pyran-4-one in the form of colorless crystals in a yield of 76.4%.

| Elementary analysis | C | H |
|---|---|---|
| Found: | 56.9% | 5.0% |
| Calcd: | 57.14 | 4.80 |

EXAMPLE 12

A 17.2 g quantity of 6-methoxy-4,5-epoxy-3-oxo-2-ethyltetrahydropyran is dissolved in 500 ml of dioxane, and 114 g of 80% aqueous solution of sulfuric acid is added dropwise to the solution with stirring. The mixture is then allowed to react with refluxing for 1 hour. The same procedure as in Example 11 is thereafter followed to obtain 10.5 g of 2-ethyl-3-oxy-4H-pyran-4-one in the form of colorless crystals in a yield of 75.6%.

| Elementary analysis | C | H |
|---|---|---|
| Found: | 60.20% | 5.95% |
| Calcd: | 59.99 | 5.75 |

EXAMPLE 13

A 20 g quantity of 6-ethoxy-4,5-epoxy-3-oxo-2-n-butyltetrahydropyran is dissolved in 500 ml of dioxane, and 114 g of 80% aqueous solution of sulfuric acid is added dropwise to the solution with stirring. The mixture is then allowed to react with refluxing for 1 hour. The same procedure as in Example 11 is thereafter followed to obtain 10.8 g of 2-n-butyl-3-oxy-4H-pyran-4-one in the form of colorless crystals in a yield of 62.5%.

| Elementary analysis | C | H |
|---|---|---|
| Found: | 64.53% | 7.45% |
| Calcd: | 64.27 | 7.19 |

EXAMPLE 14

A 22.9 g quantity of 6-ethoxy-4,5-epoxy-3-oxo-2-n-hexyltetrahydropyran is dissolved in 500 ml of dioxane, and 114 g of 80% aqueous solution of sulfuric acid is added dropwise to the solution with stirring. The mixture is then allowed to react with refluxing for 1 hour. The same procedure as in Example 11 is thereafter followed to obtain 15.3 g of 2-n-hexyl-3-oxy-4H-pyran-4-one in the form of colorless crystals in a yield of 78.4%.

| Elementary analysis | C | H |
|---|---|---|
| Found: | 67.1% | 8.20% |
| Calcd: | 67.32 | 8.22 |

EXAMPLE 15

A 28.5 g quantity of 6-ethoxy-4,5-epoxy-3-oxo-2-n-decyltetrahydropyran is dissolved in 500 ml of dioxane, and 114 g of 80% aqueous solution of sulfuric acid is added dropwise to the solution with stirring. The mixture is then allowed to react with refluxing for 1 hour. The same procedure as in Example 11 is thereafter followed to obtain 20 g of 2-n-decyl-3-oxy-4H-pyran-4-one in the form of colorless crystals in a yield of 79.5%.

| Elementary analysis | C | H |
|---|---|---|
| Found: | 71.77% | 9.58% |
| Calcd: | 71.39 | 9.59 |

EXAMPLE 16

A 15.8 g quantity of 6-ethoxy-4,5-epoxy-3-oxo-2-methyltetrahydropyran is added to 100 ml of water, and the mixture is reacted with refluxing for 24 hours. The resulting reaction mixture is distilled with steam to obtain the desired product as a distillate. The distillate is extracted with dichloromethane, and the dichloromethane layer is dried over magnesium sulfate and then concentrated at a reduced pressure to give 1.2 g of colorless crystals of 2-methyl-3-oxy-4H-pyran-4-one in a yield of 9.5%.

| Elementary analysis | C | H |
|---|---|---|
| Found: | 57.05% | 4.90% |
| Calcd: | 57.14 | 4.80 |

What we claim is:

1. A process for preparing a 3-oxy-4H-pyran-4-one derivative represented by the formula:

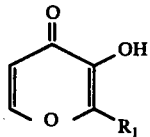

wherein $R_1$ is hydrogen or straight-chain or branched-chain alkyl having 1 to 10 carbon atoms which comprises the steps of: (1) epoxidizing a 3-oxo-3,6-dihydro-2H-pyran derivative represented by the formula:

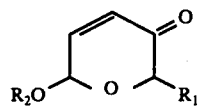

wherein $R_1$ is as defined above and $R_2$ is hydrogen, straight-chain or branched-chain alkyl having 1 to 6 carbon atoms or straight-chain or branched-chain acyl having 1 to 6 carbon atoms with a peroxide selected from the group consisting of hydrogen peroxide, trifluoroperacetic acid, perbenzoic acid, monochloroperbenzoic acid, monoperphthalic acid, tertiary butylhydroperoxide and di-tertiary butyl peroxide, in the presence of an alkaline substance at a temperature of about $-30$ to $40°$ C to obtain a 4,5-epoxy-3-oxotetrahydropyran derivative represented by the formula

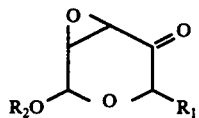

wherein $R_1$ and $R_2$ are as defined above, and (2) heating the 4,5-epoxy-3-oxotetrahydropyran derivative in the presence of an acid catalyst.

2. A process as defined in claim 1 wherein $R_2$ is straight-chain or branched-chain alkyl having 1 to 6 carbon atoms or straight-chain or branched-chain acyl having 1 to 6 carbon atoms.

3. A process as defined in claim 1 wherein the amount of alkaline substance to be used is in the range of about 0.1 to 1 mole per mole of the 3-oxo-3,6-dihydro-2H-pyran derivative.

4. A process as defined in claim 1 wherein the alkaline substance is at least one of sodium hydroxide, potassium hydroxide, sodium carbonate, potassium carbonate and basic ion-exchange resin.

5. A process as defined in claim 1 wherein the reaction temperature is in the range of about $-20°$ to $20°$ C.

6. A process as defined in claim 1 wherein the concentration of acid catalyst in the reaction system is in the range of about 0.5 to 10 w/v %.

7. A process as defined in claim 1 wherein the acid catalyst is at least one of sulfuric acid, benzene-sulfonic acid, paratoluenesulfonic acid and acid ion-exchange resin.

8. A process as defined in claim 1 wherein the heating is effected at a temperature of about $0°$ to $150°$ C.

9. A process as defined in claim 11 wherein the heating temperature is in the range of about $50°$ to $100°$ C.

10. A process as defined in claim 1 wherein the 3-oxo-3,6-dihydro-2H-pyran derivative is epoxidized in the presence of 0.1 to 1 mole of an alkaline substance per mole of the derivative, and the 4,5-epoxy-3-oxotetrahydropyran derivative is heated in the presence of 0.5 to 10 w/v % of an acid catalyst.

* * * * *

Notice of Adverse Decision in Interference

In Interference No. 99,936, involving Patent No. 4,059,595, T. Shono and Y. Matsumura, PROCESS FOR PREPARING 3-OXY-4H-PYRAN-4-ONE DERIVATIVES, final judgment adverse to the patentees was rendered June 19, 1981, as to claims 1, 3, 4, 5, 7-9.
[*Official Gazette March 7, 1989.*]